United States Patent [19]

Shuto et al.

[11] Patent Number: 5,502,242
[45] Date of Patent: Mar. 26, 1996

[54] PROPIOLATE ESTER COMPOUND AN ACARICIDE CONTAINING THE SAME AS AN ACTIVE INGREDIENT AND AN ACARICIDAL METHOD

[75] Inventors: Akira Shuto, Ashiya; Hirosi Kisida, Takarazuka; Yoji Takada, Toyonaka; Takao Ishiwatari, Minoo, all of Japan

[73] Assignee: Sumitomo Chemical Company, Limited, Osaka, Japan

[21] Appl. No.: 286,463

[22] Filed: Aug. 5, 1994

[30] Foreign Application Priority Data

Aug. 6, 1993 [JP] Japan .................................. 5-196043

[51] Int. Cl.⁶ .................................................. C07C 69/52
[52] U.S. Cl. ......................................................... 560/221
[58] Field of Search ............................ 560/221; 514/549

[56] References Cited

U.S. PATENT DOCUMENTS

| 3,097,086 | 7/1963 | Katon et al. |
| 3,100,794 | 8/1963 | Miller. |
| 3,312,541 | 4/1967 | Katon et al. ............... 71/2.6 |
| 3,996,380 | 12/1976 | Henrick. |
| 4,024,278 | 5/1977 | Henrick .................. 424/314 |
| 5,081,287 | 1/1992 | Peake et al. ............... 560/219 |

FOREIGN PATENT DOCUMENTS

| 46-3569 | 1/1971 | Japan. |
| 56-123904 | 9/1981 | Japan. |
| 58-174302 | 10/1983 | Japan. |

OTHER PUBLICATIONS

H. Yamazoe et al, "Studies on the Experimental Chemotherapy for Dermatomycosis and Candidiasis". VII., Yakugaki Zasshi, vol. 102(3), 278–284 (1982).

Mori et al, "The Nematicidal Activity of Acetylene Compounds", Agric. Biol. Chem., 46(1), 309–311, 1982.

Weber et al, "Synthesis of Acetals and Esters of Propargyl . . .", J. Stored Prod. Res., 23(1), 1–7, 1987.

Klemm et al, "Intramolecuar Diels–Alder Reactions. VI.", J. Org. Chem., vol. 36, No. 15, 1971, pp. 2169–2172.

*Primary Examiner*—Paul J. Killos
*Attorney, Agent, or Firm*—Sughrue, Mion, Zinn, Macpeak & Seas

[57] ABSTRACT

The present invention provides a propiolate ester compound represented by the formula I:

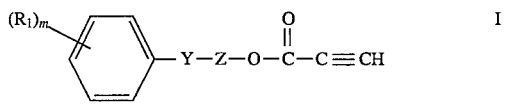

wherein $R_1$ represents a hydrogen atom, a halogen atom, a $C_1$–$C_4$ alkyl group or a $C_1$–$C_4$ alkoxy group or alkoxy group;

m denotes an integer of 1 to 5;

Y represents —$CH_2CH_2CH_2$—, —$OCH_2$— or —$CH_2O$—;

Z represents a $C_2$–$C_6$ alkylene group which may be substituted with a $C_1$–$C_4$ alkyl group; and $R_1$ may be the same or different, when m is an integer of larger than 1.

The invention also provides an acaricide containing the same as an active ingredient and an acaricidal method.

12 Claims, No Drawings

PROPIOLATE ESTER COMPOUND AN ACARICIDE CONTAINING THE SAME AS AN ACTIVE INGREDIENT AND AN ACARICIDAL METHOD

FIELD OF THE INVENTION

The present invention relates to an acaricide, and more specifically to a propiolate ester compound suitably used for controlling house dust mites.

DESCRIPTION OF THE RELATED ART

Phenyl salicylate has been known as an active ingredient of an acaricide for controlling acarine such as house dust mites. However, the controlling effect of said compound was not always satisfactory and more effective compounds were desired.

SUMMARY OF THE INVENTION

During extensive studies to develop a more effective acaricide, the present inventors have found certain novel propiolate ester compound possessing potent acaricidal activities. The present invention provides a propiolate ester compound represented by the formula I:

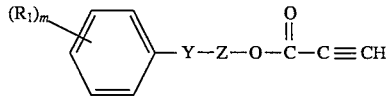

wherein $R_1$ represents a hydrogen atom, a halogen atom, a $C_1$–$C_4$ alkyl group or a $C_1$–$C_4$ alkoxy group;

m is an integer of from 1 to 5;

Y represents —$CH_2CH_2CH_2$—, —$OCH_2$— or —$CH_2O$—;

Z represents a $C_2$–$C_6$ alkylene group which may be substituted with a $C_1$–$C_4$ alkyl group; and $R_1$ may be the same or different, when m is an integer of larger than 1. It also provides an acaricidal composition containing the compound as an active ingredient and a method for controlling acarines by applying the composition.

DESCRIPTION OF THE PREFERRED EMBODIMENT

The compound of the present invention (which will be hereinafter referred to as "present compound") shows excellent quick action and residual effect, and it has good fumigating effect without offensive smell. The present compound is particularly excellent in controlling house dust mites.

Examples of the $C_1$–$C_4$ alkyl group for $R_1$ of the formula I include a methyl group, ethyl group, n-propyl group, isopropyl group, n-butyl group, isobutyl group, sec-butyl group and t-butyl group, and examples of $C_1$–$C_4$ alkoxy group for $R_1$ include methoxy group, ethoxy group, n-propyloxy group, isopropyloxy group, n-butyloxy group, isobutyloxy group, sec-butyloxy group and tert-butyloxy group.

The present compound may be produced according to one of the following methods.

Method A:

A method for producing the present compound, which comprises reacting an alcohol compound represented by the formula II:

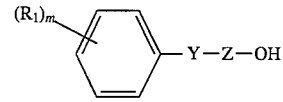

wherein $R_1$, Y, Z, and m represent those specified above, with propiolic acid chloride in the presence of a base.

The reaction is usually carried out in a solvent, which includes ethers such as diethyl ether, tetrahydrofuran and dioxane, aromatic hydrocarbons such as toluene, benzene, xylene and chlorobenzene, aliphatic or alicyclic hydrocarbons such as n-hexane, n-heptane or cyclohexane, halogenated hydrocarbons such as methylenechloride, chloroform, carbon tetrachloride and 1,2-dichloroethane, esters such as ethyl acetate and methyl acetate, alkylnitriles such as acetonitrile, a polar solvent such as N,N-dimethylformamide, N,N-dimethylacetamide, N-methylpyrrolidone, dimethylsulfoxide and pyridine, or a mixture thereof.

The reaction may be carried out in a two phase system using water as a solvent, preferably with a phase transfer catalyst such as n-tetrabutylammonium bromide and benzyltriethylammonium chloride.

The base to be used includes an organic bases such as triethylamine and pyridine, an alkali hydroxide such as sodium hydroxide or potassium hydroxide, or an alkali carbonate such as sodium carbonate or potassium carbonate.

An alkaline metal (e.g. sodium or potassium) salt of the alcohol compound represented by the formula II may be used instead of the alcohol compound and the base.

The reaction temperature is usually from –20° C. to the boiling point of the solvent used for the reaction or preferably from 0° C. to 50° C.

The amount of the propiolic acid chloride or the base to be used may be determined optionally, but is preferably 1 mole or approximately 1 mole to 1 mole of the alcohol compound II.

Method B:

A method for producing the present compound I, which comprises reacting the alcohol compound represented by the formula II above with propiolic acid. This reaction may be carried out in the presence of a dehydrating agent.

(a) Examples of the dehydrating agent used for the reaction include carbodiimides such as dicyclohexylcarbodiimide and 1-ethyl-3-(3-dimethylaminopropyl)carbodiimide, and inorganic dehydrating agents such as silicon tetrachloride. The reaction may be carried out without any solvent or in an inert organic solvent, which includes aliphatic or alicyclic hydrocarbons such as n-pentane, n-hexane, n-heptane and cyclohexane; aromatic hydrocarbons such as benzene, toluene, xylene and chlorobenzene; chlorinated hydrocarbons such as methylene chloride, chloroform, carbon tetrachloride, tetrachloroethylene or 1,2-dichloroethane and o-dichlorobenzene; esters such as methyl acetate and ethyl acetate; polar aprotic solvent such as amides (e.g. N,N-dimethylformamide, N,N-dimethylacetamide and N-methylpyrrolidone), alkylnitriles(e.g. acetonitrile) and pyridine; ethers such as diethyl ether, tetrahydrofuran and dioxane.

The reaction temperature is usually from –20° C. to 100° C. The amount of the propiolic acid compound and the dehydrating agent used to 1 mole of the alcohol compound is optionally determined, but is preferably 1 mole or approximately 1 mole.

(b) When a dehydrating agent is not used, the reaction may be carried out without any solvent or in a solvent. When the solvent is used, the solvent to be used is a polar solvent such as N,N-dimethylformamide, N,N-dimethylacetamide, N-methylpyrrolidone or dimethylsulfoxide, an aromatic hydrocarbon such as toluene, benzene, xylene or chlorobenzene. The reaction temperature is usually from 50° C. to 250° C.

An acid substance such as sulfuric acid, benzenesulfonic acid, p-toluenesulfonic acid or active silica gel may be used as a catalyst in this reaction if necessary. In this case, the amount of the catalyst is 0.0001 to 1 part by weight to one part by weight of the alcohol compound represented by the formula II. The amount of the alcohol compound II to be used to 1 mole of propiolic acid may be optionally determined, but is preferably 1 mole or approximately 1 mole.

Method C:

A method for producing the present compound, which comprises reacting a compound represented by a formula III:

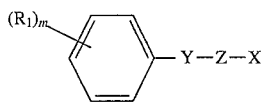

wherein $R_1$, Y, Z, and m represent the same as defined above, X is a halogen atom such as a chlorine or a bromine atom, mesyloxy group or tosyloxy group, with propiolic acid in the presence of a base.

Typical examples of the base used herein include alkali carbonates such as sodium hydrogen-carbonate, sodium carbonate and potassium carbonate.

Examples of a solvent for the reaction include ketones such as acetone and methyl ethyl ketone, ethers such as diethyl ether, tetrahydrofuran and dioxane, aromatic hydrocarbons such as benzene, toluene, xylene and chlorobenzene, aliphatic or alicyclic hydrocarbons such as n-hexane, n-heptane and cyclohexane, esters such as methyl acetate and ethyl acetate, alkylnitriles such as acetonitrile, polar aprotic solvents such as an amides (e.g. N,N-dimethylformamide, N,N-dimethylacetamide, or N-methylpyrrolidone), dimethyl sulfoxide and pyridine; and mixture thereof.

The reaction temperature is usually from −20° C. to 100° C. or preferably from 0° C. to 50° C.

The amount of the alcohol compound and the base to be used may be determined optionally, but is preferably 1 mole or approximately 1 mole to the propiolic acid compound.

An alkaline metal salt (for example, sodium or potassium) of propiolic acid may be used instead of propiolic acid. In this case, the base is not always required.

Method D:

A method for producing the present invention compound, which comprises reacting an ester compound represented by the formula IV:

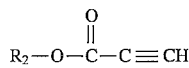

wherein $R_2$ represents $C_1$–$C_3$ alkyl group, such as methyl group, ethyl group and n-propyl group, with the alcohol compound represented by the formula II in the presence of a catalyst.

The reaction may be carried out in a solvent or without using a solvent. The solvent to be used includes an ether such as diethyl ether, tetrahydrofuran or dioxane, an aromatic hydrocarbon such as toluene, benzene, xylene or chlorobenzene, an aliphatic or alicyclic hydrocarbon such as n-hexane, n-heptane and cyclohexane, or a halogenated hydrocarbon such as methylene chloride, chloroform, carbon tetrachloride and 1,2-dichloroethane.

Examples of the catalyst used herein include acid substances such as sulfuric acid, p-toluenesulfonic acid and benzenesulfonic acid.

The reaction temperature is usually from 50° C. to the boiling point of the solvent used for the reaction or 200°. The amount of the alcohol compound represented by the formula II to be used to one mole of the ester compound represented by the formula IV may be determined optionally. However, preferably at least two moles of the alcohol compound are used to one mole of the ester compound, and 0.0001 to 1 part by weight of the catalyst is used to 1 part by weight of the ester compound.

In any of the above methods, after the completion of the reaction, the present compound is isolated by a conventional post-treatment such as solvent extraction and concentration. The present compound obtained may be purified by column chromatography, distillation, re-crystallization or the like if necessary.

When the present compound has asymmetric carbon atoms, the present compound includes every optically active isomer ((+)- and (−)- isomers) and mixtures thereof in an optional ratio.

In the alcohol compounds represented by the formula II, an alcohol compound having —$CH_2CH_2CH_2$— for Y may be prepared from a corresponding carboxylic acid compound by reducing the compound with a reducing agent, such as lithium aluminum hydride or borane THF complex. Commercially available alcohol compounds can be used in the present method. The carboxylic acid compound is obtained by a method specified in Bulletin of the Chemical Society of Japan Vol. 88, No. 6 (1967), Org. Synth., I, 436 (1941), or Org. Synth., II, 474 (1943). In the alcohol compound represented by the formula II, an alcohol compound having —$OCH_2$— for Y may be prepared from a corresponding ester compound by using a reducing agent such as lithium aluminum hydride. The ester compound is obtained by a method described in Synth. Commun. 14, 69 (1984), or the alcohol compound may be prepared from the corresponding phenol and a haloalcohol by a known method. In the alcohol compound represented by the formula II, those having —$CH_2O$— for Y may be prepared by a method described in J. Am. Chem. Soc., 60, 1472 (1938).

The compound represented by the formula III may be prepared from the alcohol compound represented by the formula II by a known method. The compound having —$OCH_2$— for Y may be prepared by a method described in Org. Synth., I, 435 (1941).

The alkaline metal salt of propiolic acid which may be used in the method C and propiolic acid chloride used in the method A are prepared by a method described in J. Org. Chem., 36, 2169 (1971).

Table 1 shows examples of the present compound (substituents of the compound represented by the formula I are listed), though it is not construed to limit the present invention thereto.

TABLE 1

| Examples of the present compound represented by the formula I | | |
|---|---|---|
| $(R_1)_m$ | Y | Z |
| H | $(CH_2)_3$ | $(CH_2)_3$ |
| H | $(CH_2)_3$ | $(CH_2)_4$ |
| H | $(CH_2)_3$ | $(CH_2)_5$ |
| H | $(CH_2)_3$ | $(CH_2)_6$ |
| H | $(CH_2)_3$ | $(CH_2)_7$ |

TABLE 1-continued

Examples of the present compound represented by the formula I

| $(R_1)_m$ | Y | Z |
|---|---|---|
| 4-Cl | $-(CH_2)_3-$ | $-CH(CH_3)-CH_2-$ |
| 4-Cl | $-(CH_2)_3-$ | $-CH_2-CH(CH_3)-CH_2-$ |
| H | $-(CH_2)_3-$ | $-CH(CH_3)-CH_2-$ |
| H | $-(CH_2)_3-$ | $-CH_2-CH(CH_3)-CH_2-$ |
| H | $-(CH_2)_3-$ | $-(CH_2)_2-CH(CH_3)-CH_2-$ |
| H | $-(CH_2)_3-$ | $-CH(C_2H_5)-CH_2-$ |
| H | $-(CH_2)_3-$ | $-(CH_2)_2-CH(C_2H_5)-CH_2-$ |
| H | $-(CH_2)_3-$ | $-CH_2-CH(n-C_3H_7)-CH_2-$ |
| H | $-(CH_2)_3-$ | $-CH_2-CH(i-C_3H_7)-CH_2-$ |
| H | $-(CH_2)_3-$ | $-CH_2-CH(n-C_4H_9)-CH_2-$ |
| H | $-(CH_2)_3-$ | $-CH_2-CH(CH_3)-(CH_2)_2-$ |
| H | $-(CH_2)_3-$ | $-(CH_2)_3-CH(CH_3)-CH_2-$ |
| H | $-(CH_2)_3-$ | $-CH_2-CH(CH_3)-(CH_2)_3-$ |
| H | $-(CH_2)_3-$ | $-CH(CH_3)-(CH_2)_4-$ |
| H | $-(CH_2)_3-$ | $-(CH_2)_2-CH(CH_3)-(CH_2)_3-$ |
| H | $-(CH_2)_3-$ | $-(CH_2)_2-CH(CH_3)-(CH_2)_2-$ |
| H | $-(CH_2)_3-$ | $-(CH_2)_3-CH(CH_3)-(CH_2)_2-$ |
| H | $-(CH_2)_3-$ | $-CH_2-CH(CH_3)-(CH_2)_2-$ |
| H | $-(CH_2)_3-$ | $-CH(CH_2)-(CH_2)_5-$ |
| 4-Cl | $-(CH_2)_3-$ | $-(CH_2)_2-CH(CH_3)-CH_2-$ |
| 4-Cl | $-(CH_2)_3-$ | $-CH(CH_3)-(CH_2)_3-$ |
| 4-Cl | $-(CH_2)_3-$ | $-CH(C_2H_5)-(CH_2)_3-$ |
| 4-Cl | $-(CH_2)_3-$ | $-CH_2-CH(C_2H_5)-CH_2-$ |
| 4-Cl | $-(CH_2)_3-$ | $-(CH_2)_2-CH(C_2H_5)-CH_2$ |
| H | $-(CH_2)_3-$ | $-CH_2-CH(C_2H_5)-CH_2-$ |
| H | $-(CH_2)_3-$ | $-(CH_2)_3-CH(C_2H_5)-CH_2-$ |
| H | $-(CH_2)_3-$ | $-CH_2-CH(C_2H_5)-(CH_2)_2-$ |
| H | $-(CH_2)_3-$ | $-CH(C_2H_5)-(CH_2)_2-$ |
| 4-Cl | $-(CH_2)_3-$ | $-CH(C_2H_5)-(CH_2)_2-$ |
| H | $-(CH_2)_3-$ | $-(CH_2)_2-CH(C_2H_5)-(CH_2)_3-$ |
| H | $-(CH_2)_3-$ | $-(CH_2)_3-CH(C_2H_5)-(CH_2)_2-$ |
| 4-CH$_3$ | $-(CH_2)_3-$ | $-(CH_2)_4-$ |
| 3-CH$_3$ | $-(CH_2)_3-$ | $-(CH_2)_4-$ |
| 2-CH$_3$ | $-(CH_2)_3-$ | $-(CH_2)_4-$ |
| 4-CH$_3$ | $-(CH_2)_3-$ | $-(CH_2)_2-$ |
| 3-CH$_3$ | $-(CH_2)_3-$ | $-(CH_2)_2-$ |
| 2-CH$_3$ | $-(CH_2)_3-$ | $-(CH_2)_2-$ |
| 4-CH$_3$ | $-(CH_2)_3-$ | $-(CH_2)_5-$ |
| 3-CH$_3$ | $-(CH_2)_3-$ | $-(CH_2)_5-$ |
| 2-CH$_3$ | $-(CH_2)_3-$ | $-(CH_2)_5-$ |
| 2,4-(CH$_3$)$_2$ | $-(CH_2)_3-$ | $-(CH_2)_3-$ |
| 4-i-C$_3$H$_7$ | $-(CH_2)_3-$ | $-(CH_2)_3-$ |
| 4-n-C$_4$H$_9$ | $-(CH_2)_3-$ | $-(CH_2)_3-$ |
| 4-C$_2$H$_5$ | $-(CH_2)_3-$ | $-(CH_2)_4-$ |
| 2,4,6-(CH$_3$)$_3$ | $-(CH_2)_3-$ | $-(CH_2)_4-$ |
| 4-F | $-(CH_2)_3-$ | $-(CH_2)_4-$ |

TABLE 1-continued

Examples of the present compound represented by the formula I

| $(R_1)_m$ | Y | Z |
|---|---|---|
| 2-Cl | $(CH_2)_3$ | $(CH_2)_4$ |
| 3-Cl | $(CH_2)_3$ | $(CH_2)_4$ |
| 2,3-Cl$_2$ | $(CH_2)_3$ | $(CH_2)_4$ |
| 3,4-Cl$_2$ | $(CH_2)_3$ | $(CH_2)_4$ |
| 2,6-Cl$_2$ | $(CH_2)_3$ | $(CH_2)_4$ |
| 3,5-Cl$_2$ | $(CH_2)_3$ | $(CH_2)_4$ |
| 2-OCH$_3$ | $(CH_2)_3$ | $(CH_2)_4$ |
| 3-OCH$_3$ | $(CH_2)_3$ | $(CH_2)_4$ |
| 4-OCH$_3$ | $(CH_2)_3$ | $(CH_2)_4$ |
| 4-OC$_2$H$_5$ | $(CH_2)_3$ | $(CH_2)_4$ |
| 3-OC$_2$H$_5$ | $(CH_2)_3$ | $(CH_2)_4$ |
| 2,3-(CH$_3$)$_2$, 4-OCH$_3$ | $(CH_2)_3$ | $(CH_2)_4$ |
| 3-CH$_3$, 4-OCH$_3$ | $(CH_2)_3$ | $(CH_2)_4$ |
| 2,3,5-Cl$_3$ | $(CH_2)_3$ | $(CH_2)_4$ |
| 2,3,6-Cl$_3$ | $(CH_2)_3$ | $(CH_2)_4$ |
| 2,3,4-Cl$_3$ | $(CH_2)_3$ | $(CH_2)_4$ |
| 4-n-C$_3$H$_7$ | $(CH_2)_3$ | $(CH_2)_4$ |
| 4-Cl | $(CH_2)_3$ | $(CH_2)_2$ |
| 3,4-Cl$_2$ | $(CH_2)_3$ | $(CH_2)_2$ |
| 4-Cl | $(CH_2)_3$ | $(CH_2)_3$ |
| 3-Cl | $(CH_2)_3$ | $(CH_2)_3$ |
| 2-Cl | $(CH_2)_3$ | $(CH_2)_3$ |
| 3,4-Cl$_2$ | $(CH_2)_3$ | $(CH_2)_3$ |
| 4-Cl | $(CH_2)_3$ | $(CH_2)_4$ |
| 4-Cl | $(CH_2)_3$ | $(CH_2)_5$ |
| 4-Cl | $(CH_2)_3$ | $(CH_2)_6$ |
| 4-F | $(CH_2)_3$ | $(CH_2)_4$ |
| 4-F | $(CH_2)_3$ | $(CH_2)_5$ |
| 4-F | $(CH_2)_3$ | $(CH_2)_6$ |
| 3,4-F$_2$ | $(CH_2)_3$ | $(CH_2)_2$ |
| 3,4-F$_2$ | $(CH_2)_3$ | $(CH_2)_6$ |
| 4-CH$_3$ | $(CH_2)_3$ | $(CH_2)_5$ |
| 4-CH$_3$ | $(CH_2)_3$ | $(CH_2)_4$ |
| 4-CH$_3$ | $(CH_2)_3$ | $-\text{CH}(\text{CH}_3)-\text{CH}_2-$ |
| 4-CH$_3$ | $(CH_2)_3$ | $-\text{CH}(\text{C}_2\text{H}_5)-\text{CH}_2-$ |
| 4-F | $(CH_2)_3$ | $-\text{CH}_2-\text{CH}(\text{CH}_3)-\text{CH}_2-$ |
| 4-CH$_3$ | $(CH_2)_3$ | $(CH_2)_2\text{CH}(\text{CH}_3)-\text{CH}_2-$ |
| 4-CH$_3$ | $(CH_2)_3$ | $-\text{CH}_2-\text{CH}(\text{C}_2\text{H}_5)-\text{CH}_2-$ |
| 4-CH$_3$ | $(CH_2)_3$ | $-\text{CH}(\text{CH}_3)-\text{CH}_2-$ |
| 4-CH$_3$ | $(CH_2)_3$ | $(CH_2)_3\text{CH}(\text{CH}_3)-\text{CH}_2-$ |
| 4-CH$_3$ | $(CH_2)_3$ | $-\text{CH}_2-\text{CH}(\text{CH}_3)(CH_2)_3$ |
| 4-CH$_3$ | $(CH_2)_3$ | $-\text{CH}(\text{CH}_3)(CH_2)_2$ |
| 4-CH$_3$ | $(CH_2)_3$ | $-\text{CH}_2-\text{CH}(\text{CH}_3)(CH_2)_2$ |
| 4-CH$_3$ | $(CH_2)_3$ | $(CH_2)_2\text{CH}(\text{CH}_3)(CH_2)_2$ |
| 4-CH$_3$ | $(CH_2)_3$ | $-\text{CH}_2-\text{CH}(\text{CH}_3)(CH_2)_3$ |
| 3-CH$_3$ | $(CH_2)_3$ | $-\text{CH}_2-\text{CH}(\text{CH}_3)-\text{CH}_2-$ |
| 3-CH$_3$ | $(CH_2)_3$ | $-\text{CH}(\text{CH}_3)(CH_2)_2$ |
| 4-CH$_3$ | $(CH_2)_3$ | $(CH_2)_2\text{CH}(\text{CH}_3)(CH_2)_3$ |
| 4-CH$_3$ | $(CH_2)_3$ | $(CH_2)_4\text{CH}(\text{CH}_3)-\text{CH}_2-$ |
| 4-F | $(CH_2)_3$ | $-\text{CH}(\text{CH}_3)(CH_2)_3$ |
| 4-F | $(CH_2)_3$ | $-\text{CH}(\text{C}_2\text{H}_5)(CH_2)_3$ |
| 4-CH$_3$ | $(CH_2)_3$ | $-\text{CH}_2-\text{CH}(\text{C}_2\text{H}_5)-\text{CH}_2-$ |
| 4-CH$_3$ | $(CH_2)_3$ | $-\text{CH}_2-\text{CH}(\text{C}_2\text{H}_5)(CH_2)_2$ |
| 4-CH$_3$ | $(CH_2)_3$ | $(CH_2)_2\text{CH}(\text{C}_2\text{H}_5)(CH_2)_2$ |

TABLE 1-continued

Examples of the present compound represented by the formula I

| $(R_1)_m$ | Y | Z |
|---|---|---|
| 4-CH$_3$ | $-(CH_2)_3-$ | $-(CH_2)_2-CH(C_2H_5)-CH_2-$ |
| 4-CH$_3$ | $-(CH_2)_3-$ | $-CH_2-CH(C_2H_5)-(CH_2)_3-$ |
| 4-CH$_3$ | $-(CH_2)_3-$ | $-CH(C_2H_5)-(CH_2)_3-$ |
| 4-CH$_3$ | $-(CH_2)_3-$ | $-CH(C_2H_5)-(CH_2)_4-$ |
| 4-CH$_3$ | $-(CH_2)_3-$ | $-(CH_2)_2-CH(C_2H_5)-(CH_2)_3-$ |
| 4-CH$_3$ | $-(CH_2)_3-$ | $-(CH_2)_3-CH(C_2H_5)-(CH_2)_2-$ |
| 2,6-(i-C$_3$H$_7$)$_2$ | $-(CH_2)_3-$ | $-(CH_2)_2-$ |
| 2,6-(t-C$_4$H$_9$)$_2$ | $-(CH_2)_3-$ | $-(CH_2)_2-$ |
| 2,6-(sec-C$_4$H$_9$)$_2$ | $-(CH_2)_3-$ | $-(CH_2)_2-$ |
| H | $-OCH_2-$ | $-(CH_2)_2-$ |
| H | $-OCH_2-$ | $-(CH_2)_3-$ |
| H | $-OCH_2-$ | $-(CH_2)_4-$ |
| H | $-OCH_2-$ | $-(CH_2)_5-$ |
| H | $-OCH_2-$ | $-(CH_2)_6-$ |
| 4-CH$_3$ | $-OCH_2-$ | $-CH_2-CH(CH_3)-$ |
| 4-CH$_3$ | $-OCH_2-$ | $-CH(CH_3)-CH_2-$ |
| H | $-OCH_2-$ | $-CH_2-CH(CH_3)-$ |
| H | $-OCH_2-$ | $-CH(CH_3)-CH_2-$ |
| H | $-OCH_2-$ | $-CH_2-CH(CH_3)-CH_2-$ |
| H | $-OCH_2-$ | $-CH_2-CH(C_2H_5)-CH_2-$ |
| H | $-OCH_2-$ | $-CH_2-CH(C_2H_5)-(CH_2)_2-$ |
| H | $-OCH_2-$ | $-CH_2-CH(n-C_3H_7)-CH_2-$ |
| H | $-OCH_2-$ | $-CH_2CH(i-C_3H_7)-CH_2-$ |
| H | $-OCH_2-$ | $-CH_2-CH(n-C_4H_9)-CH_2-$ |
| H | $-OCH_2-$ | $-(CH_2)_3-CH(CH_3)-CH_2-$ |
| H | $-OCH_2-$ | $-CH_2-CH(CH_3)-(CH_2)_3-$ |
| H | $-OCH_2-$ | $-CH(CH_3)-(CH_2)_2-$ |
| H | $-OCH_2-$ | $-(CH_2)_2-CH(CH_3)-CH_2-$ |
| H | $-OCH_2-$ | $-CH_2-CH(CH_3)-(CH_2)_2-$ |
| H | $-OCH_2-$ | $-(CH_2)_2-CH(CH_3)-$ |
| H | $-OCH_2-$ | $-CH_2-CH(CH_3)-(CH_2)_2-$ |
| H | $-OCH_2-$ | $-CH(CH_3)-(CH_2)_5-$ |
| 4-CH$_3$ | $-OCH_2-$ | $-CH_2-CH(CH_3)-CH_2-$ |
| 4-CH$_3$ | $-OCH_2-$ | $-CH(CH_3)-(CH_2)_4-$ |
| 4-CH$_3$ | $-OCH_2-$ | $-CH(CH_3)-(CH_2)_3-$ |
| 4-CH$_3$ | $-OCH_2-$ | $-CH_2-CH(C_2H_5)-CH_2-$ |
| 4-CH$_3$ | $-OCH_2-$ | $-(CH_2)_2-CH(C_2H_5)-CH_2-$ |
| H | $-OCH_2-$ | $-CH_3-CH(C_2H_5)-CH_2-$ |
| H | $-OCH_2-$ | $-(CH_2)_2-CH(C_2H_5)-CH_2-$ |
| H | $-OCH_2-$ | $-CH_2-CH(C_2H_5)-(CH_2)_2-$ |
| H | $-OCH_2-$ | $-CH_2-CH(C_2H_5)-(CH_2)_2-$ |
| H | $-OCH_2-$ | $-(CH_2)_3-CH(C_2H_5)-CH_2-$ |
| 4-CH$_3$ | $-OCH_2-$ | $-(CH_2)_2-$ |
| 3-CH$_3$ | $-OCH_2-$ | $-(CH_2)_2-$ |

TABLE 1-continued

Examples of the present compound represented by the formula I

| $(R_1)_m$ | Y | Z |
|---|---|---|
| 2-$CH_3$ | $-OCH_2-$ | $-(CH_2)_2-$ |
| 4-$CH_3$ | $-OCH_2-$ | $-(CH_2)_3-$ |
| 3-$CH_3$ | $-OCH_2-$ | $-(CH_2)_3-$ |
| 2-$CH_3$ | $-OCH_2-$ | $-(CH_2)_3-$ |
| 4-$CH_3$ | $-OCH_2-$ | $-(CH_2)_4-$ |
| 3-$CH_3$ | $-OCH_2-$ | $-(CH_2)_4-$ |
| 2-$CH_3$ | $-OCH_2-$ | $-(CH_2)_4-$ |
| 2,4-$(CH_3)_2$ | $-OCH_2-$ | $-(CH_2)_3-$ |
| 4-i-$C_3H_7$ | $-OCH_2-$ | $-(CH_2)_3-$ |
| 4-n-$C_4H_9$ | $-OCH_2-$ | $-(CH_2)_3-$ |
| 4-$C_2H_5$ | $-OCH_2-$ | $-(CH_2)_3-$ |
| 2,4,6-$(CH_3)_3$ | $-OCH_2-$ | $-(CH_2)_3-$ |
| 4-F | $-OCH_2-$ | $-(CH_2)_3-$ |
| 4-$C_2H_5$ | $-OCH_2-$ | $-(CH_2)_2-$ |
| 2-Cl | $-OCH_2-$ | $-(CH_2)_3-$ |
| 3-Cl | $-OCH_2-$ | $-(CH_2)_3-$ |
| 2,3-$Cl_2$ | $-OCH_2-$ | $-(CH_2)_3-$ |
| 3,4-$Cl_2$ | $-OCH_2-$ | $-(CH_2)_3-$ |
| 2,6-$Cl_2$ | $-OCH_2-$ | $-(CH_2)_3-$ |
| 3,5-$Cl_2$ | $-OCH_2-$ | $-(CH_2)_3-$ |
| 2-$OCH_3$ | $-OCH_2-$ | $-(CH_2)_3-$ |
| 3-$OCH_3$ | $-OCH_2-$ | $-(CH_2)_3-$ |
| 4-$OCH_3$ | $-OCH_2-$ | $-(CH_2)_3-$ |
| 4-$OC_2H_5$ | $-OCH_2-$ | $-(CH_2)_3-$ |
| 3-$OC_2H_5$ | $-OCH_2-$ | $-(CH_2)_3-$ |
| 2,3-$(CH_3)_2$, 4-$OCH_3$ | $-OCH_2-$ | $-(CH_2)_3-$ |
| 3-$CH_3$, 4-$OCH_3$ | $-OCH_2-$ | $-(CH_2)_3-$ |
| 2,3,5-$Cl_3$ | $-OCH_2-$ | $-(CH_2)_3-$ |
| 2,3,6-$Cl_3$ | $-OCH_2-$ | $-(CH_2)_3-$ |
| 2,3,4-$Cl_3$ | $-OCH_2-$ | $-(CH_2)_3-$ |
| 4-n-$C_3H_7$ | $-OCH_2-$ | $-(CH_2)_3-$ |
| 4-Cl | $-OCH_2-$ | $-(CH_2)_3-$ |
| 3,4-$Cl_2$ | $-OCH_2-$ | $-(CH_2)_2-$ |
| 4-Cl | $-OCH_2-$ | $-(CH_2)_2-$ |
| 3-Cl | $-OCH_2-$ | $-(CH_2)_2-$ |
| 2-Cl | $-OCH_2-$ | $-(CH_2)_2-$ |
| 3,4-$Cl_2$ | $-OCH_2-$ | $-(CH_2)_4-$ |
| 2,6-$(CH_3)_2$ | $-OCH_2-$ | $-(CH_2)_2-$ |
| 4-Cl | $-OCH_2-$ | $-(CH_2)_4-$ |
| 4-Cl | $-OCH_2-$ | $-(CH_2)_5-$ |
| 4-Cl | $-OCH_2-$ | $-(CH_2)_6-$ |
| 4-$CH_3$ | $-OCH_2-$ | $-(CH_2)_5-$ |
| 4-F | $-OCH_2-$ | $-(CH_2)_2-$ |
| 4-F | $-OCH_2-$ | $-(CH_2)_4-$ |
| 4-F | $-OCH_2-$ | $-(CH_2)_5-$ |
| 4-F | $-OCH_2-$ | $-(CH_2)_6-$ |
| 3,4-$F_2$ | $-OCH_2-$ | $-(CH_2)_3-$ |
| 3,4-$F_2$ | $-OCH_2-$ | $-(CH_2)_4-$ |
| 4-$CH_3$ | $-OCH_2-$ | $-(CH_2)_6-$ |
| 4-$CH_3$ | $-OCH_2-$ | $-CH_2-CH(CH_3)-$ |
| 4-$CH_3$ | $-OCH_2-$ | $-CH_2-CH(C_2H_5)-CH_2-$ |
| 4-F | $-OCH_2-$ | $-CH_2-CH(CH_3)-CH_2-$ |
| 4-$CH_3$ | $-OCH_2-$ | $-(CH_2)_2-CH(CH_3)-CH_2-$ |
| 4-$CH_3$ | $-OCH_2-$ | $-(CH_2)_2-CH(C_2H_5)-CH_2-$ |
| 4-$CH_3$ | $-OCH_2-$ | $-CH_2-CH(CH_3)-(CH_2)_2-$ |
| 4-$CH_3$ | $-OCH_2-$ | $-(CH_2)_3-CH(CH_3)-(CH_2)_2-$ |
| 4-$CH_3$ | $-OCH_2-$ | $-CH_2-CH(CH_3)-(CH_2)_3-$ |
| 4-$CH_3$ | $-OCH_2-$ | $-CH(CH_3)-(CH_2)_2-$ |
| 4-$CH_3$ | $-OCH_2-$ | $-(CH_2)_2-CH(CH_3)-(CH_2)_2-$ |
| 4-$CH_3$ | $-OCH_2-$ | $-(CH_2)_2-CH(CH_3)-(CH_2)_3-$ |
| 3-$CH_3$ | $-OCH_2-$ | $-CH_2-CH(CH_3)-CH_2-$ |
| 3-$CH_3$ | $-OCH_2-$ | $-CH_2-CH(CH_3)-(CH_2)_2-$ |
| 3-$CH_3$ | $-OCH_2-$ | $-CH(CH_3)-(CH_2)_3-$ |
| 3-$CH_3$ | $-OCH_2-$ | $-CH_2-CH(CH_3)-(CH_2)_3-$ |

TABLE 1-continued

Examples of the present compound represented by the formula I

| $(R_1)_m$ | Y | Z |
|---|---|---|
| 4-CH$_3$ | —OCH$_2$— | —(CH$_2$)$_4$—CH(CH$_3$)—CH$_2$— |
| 4-F | —OCH$_2$— | —CH(CH$_3$)—(CH$_2$)$_4$— |
| 4-CH$_3$ | —OCH$_2$— | —CH$_2$—CH(C$_2$H$_5$)—CH$_2$— |
| 4-CH$_3$ | —OCH$_2$— | —CH$_2$—CH(C$_2$H$_5$)—CH$_2$— |
| 4-CH$_3$ | —OCH$_2$— | —(CH$_2$)$_2$—CH(C$_2$H$_5$)—(CH$_2$)$_2$— |
| 4-CH$_3$ | —OCH$_2$— | —(CH$_2$)$_3$—CH(C$_2$H$_5$)—CH$_2$— |
| 4-CH$_3$ | —OCH$_2$— | —CH$_2$—CH(C$_2$H$_5$)—(CH$_2$)$_3$— |
| 4-CH$_3$ | —OCH$_2$— | —(CH$_2$)$_2$—CH(C$_2$H$_5$)—(CH$_2$)$_3$— |
| 4-CH$_3$ | —OCH$_2$— | —(CH$_2$)$_3$—CH(C$_2$H$_5$)—(CH$_2$)$_2$— |
| 2,6-(i-C$_3$H$_7$)$_2$ | —OCH$_2$— | —(CH$_2$)$_3$— |
| 2,6-(i-C$_3$H$_7$)$_2$ | —OCH$_2$— | —(CH$_2$)$_2$— |
| 2,6-(i-C$_4$H$_9$)$_2$ | —OCH$_2$— | —(CH$_2$)$_2$— |
| 2,6-(sec-C$_4$H$_9$)$_2$ | —OCH$_2$— | —(CH$_2$)$_2$— |
| H | —CH$_2$O— | —(CH$_2$)$_2$— |
| H | —CH$_2$O— | —(CH$_2$)$_3$— |
| H | —CH$_2$O— | —(CH$_2$)$_4$— |
| H | —CH$_2$O— | —(CH$_2$)$_5$— |
| H | —CH$_2$O— | —(CH$_2$)$_6$— |
| H | —CH$_2$O— | —CH$_2$—CH(CH$_3$)— |
| H | —CH$_2$O— | —(CH$_2$)$_2$—CH(CH$_3$)— |
| H | —CH$_2$O— | —(CH$_2$)$_3$—CH(CH$_3$)— |
| H | —CH$_2$O— | —(CH$_2$)$_4$—CH(CH$_3$)— |
| H | —CH$_2$O— | —(CH$_2$)$_5$—CH(CH$_3$)— |
| H | —CH$_2$O— | —CH$_2$—CH(C$_2$H$_5$)—CH$_2$— |
| H | —CH$_2$O— | —(CH$_2$)$_2$—CH(C$_2$H$_5$)—CH$_2$— |
| H | —CH$_2$O— | —(CH$_2$)$_2$—CH(n-C$_3$H$_7$)—CH$_2$— |
| H | —CH$_2$O— | —(CH$_2$)$_2$—CH(i-C$_3$H$_7$)—CH$_2$— |
| H | —CH$_2$O— | —(CH$_2$)$_2$—CH(n-C$_4$H$_9$)—CH$_2$— |
| H | —CH$_2$O— | —CH$_2$—CH(CH$_3$)—CH$_2$— |
| H | —CH$_2$O— | —CH(CH$_3$)—CH$_2$— |
| H | —CH$_2$O— | —(CH$_2$)$_3$—CH(CH$_3$)—CH$_2$— |
| H | —CH$_2$O— | —CH$_2$—CH(CH$_3$)—(CH$_2$)$_3$— |
| H | —CH$_2$O— | —(CH$_2$)$_2$—CH(CH$_3$)—CH$_2$— |
| H | —CH$_2$O— | —CH$_2$—CH(CH$_3$)—(CH$_2$)$_2$— |
| H | —CH$_2$O— | —(CH$_2$)$_4$—CH(CH$_3$)—CH$_2$— |
| H | —CH$_2$O— | —CH(CH$_3$)—(CH$_2$)$_5$— |
| 4-CH$_3$ | —CH$_2$O— | —CH$_2$—CH(CH$_3$)—CH$_2$— |
| 4-CH$_3$ | —CH$_2$O— | —CH(CH$_3$)—CH$_2$— |
| 4-CH$_3$ | —CH$_2$O— | —CH(C$_2$H$_5$)—(CH$_2$)$_4$— |
| 4-CH$_3$ | —CH$_2$O— | —CH$_2$—CH(C$_2$H$_5$)—CH$_2$— |
| 4-CH$_3$ | —CH$_2$O— | —(CH$_2$)$_2$—CH(C$_2$H$_5$)—CH$_2$— |
| H | —CH$_2$O— | —CH$_2$—CH(C$_2$H$_5$)—CH$_2$— |
| H | —CH$_2$O— | —(CH$_2$)$_2$—CH(C$_2$H$_5$)—CH$_2$— |
| H | —CH$_2$O— | —CH$_2$—CH(C$_2$H$_5$)—(CH$_2$)$_2$— |

TABLE 1-continued

Examples of the present compound represented by the formula I

| $(R_1)_m$ | Y | Z |
|---|---|---|
| H | $-CH_2O-$ | $-CH(C_2H_5)(CH_2)_4-$ |
| 4-Cl | $-CH_2O-$ | $-CH(C_2H_5)(CH_2)_4-$ |
| H | $-CH_2O-$ | $-CH_2-CH(C_2H_5)(CH_2)_2-$ |
| H | $-CH_2O-$ | $-(CH_2)_3CH(C_2H_5)-$ |
| 4-CH$_3$ | $-CH_2O-$ | $-(CH_2)_2-$ |
| 3-CH$_3$ | $-CH_2O-$ | $-(CH_2)_2-$ |
| 2-CH$_3$ | $-CH_2O-$ | $-(CH_2)_2-$ |
| 4-CH$_3$ | $-CH_2O-$ | $-(CH_2)_3-$ |
| 3-CH$_3$ | $-CH_2O-$ | $-(CH_2)_3-$ |
| 2-CH$_3$ | $-CH_2O-$ | $-(CH_2)_3-$ |
| 4-CH$_3$ | $-CH_2O-$ | $-(CH_2)_4-$ |
| 3-CH$_3$ | $-CH_2O-$ | $-(CH_2)_4-$ |
| 2-CH$_3$ | $-CH_2O-$ | $-(CH_2)_4-$ |
| 2,4-(CH$_3$)$_2$ | $-CH_2O-$ | $-(CH_2)_2-$ |
| 4-i-C$_3$H$_7$ | $-CH_2O-$ | $-(CH_2)_2-$ |
| 4-n-C$_4$H$_9$ | $-CH_2O-$ | $-(CH_2)_2-$ |
| 4-C$_2$H$_5$ | $-CH_2O-$ | $-(CH_2)_2-$ |
| 2,4,6-(CH$_3$)$_3$ | $-CH_2O-$ | $-(CH_2)_2-$ |
| 4-F | $-CH_2O-$ | $-(CH_2)_2-$ |
| 2-Cl | $-CH_2O-$ | $-(CH_2)_2-$ |
| 3-Cl | $-CH_2O-$ | $-(CH_2)_2-$ |
| 2,3-Cl$_2$ | $-CH_2O-$ | $-(CH_2)_2-$ |
| 3,4-Cl$_2$ | $-CH_2O-$ | $-(CH_2)_2-$ |
| 2,6-Cl$_2$ | $-CH_2O-$ | $-(CH_2)_2-$ |
| 3,5-Cl$_2$ | $-CH_2O-$ | $-(CH_2)_2-$ |
| 2-OCH$_3$ | $-CH_2O-$ | $-(CH_2)_2-$ |
| 3-OCH$_3$ | $-CH_2O-$ | $-(CH_2)_2-$ |
| 4-OCH$_3$ | $-CH_2O-$ | $-(CH_2)_2-$ |
| 4-OC$_2$H$_5$ | $-CH_2O-$ | $-(CH_2)_2-$ |
| 3-OC$_2$H$_5$ | $-CH_2O-$ | $-(CH_2)_2-$ |
| 2,3-(CH$_3$)$_2$, 4-OCH$_3$ | $-CH_2O-$ | $-(CH_2)_2-$ |
| 3-CH$_3$, 4-OCH$_3$ | $-CH_2O-$ | $-(CH_2)_2-$ |
| 2,3,5-Cl$_3$ | $-CH_2O-$ | $-(CH_2)_2-$ |
| 2,3,6-Cl$_3$ | $-CH_2O-$ | $-(CH_2)_2-$ |
| 2,3,4-Cl$_3$ | $-CH_2O-$ | $-(CH_2)_2-$ |
| 4-n-C$_3$H$_7$ | $-CH_2O-$ | $-(CH_2)_2-$ |
| 4-Cl | $-OCH_2-$ | $-(CH_2)_2-$ |
| 3,4-Cl$_2$ | $-OCH_2-$ | $-(CH_2)_2-$ |
| 4-Cl | $-OCH_2-$ | $-(CH_2)_2-$ |
| 3-Cl | $-OCH_2-$ | $-(CH_2)_3-$ |
| 2-Cl | $-OCH_2-$ | $-(CH_2)_3-$ |
| 3,4-Cl$_2$ | $-OCH_2-$ | $-(CH_2)_3-$ |
| 4-Cl | $-OCH_2-$ | $-(CH_2)_4-$ |
| 4-Cl | $-OCH_2-$ | $-(CH_2)_5-$ |
| 4-Cl | $-OCH_2-$ | $-(CH_2)_6-$ |
| 4-F | $-OCH_2-$ | $-(CH_2)_4-$ |
| 4-F | $-OCH_2-$ | $-(CH_2)_5-$ |
| 4-F | $-OCH_2-$ | $-(CH_2)_6-$ |
| 3,4-F$_2$ | $-OCH_2-$ | $-(CH_2)_2-$ |
| 3,4-F$_2$ | $-OCH_2-$ | $-(CH_2)_6-$ |
| 4-CH$_3$ | $-OCH_2-$ | $-(CH_2)_5-$ |
| 4-CH$_3$ | $-OCH_2-$ | $-(CH_2)_6-$ |
| 4-CH$_3$ | $-OCH_2-$ | $-(CH_2)_2CH(CH_3)-CH_2-$ |
| 4-CH$_3$ | $-CH_2O-$ | $-(CH_2)_2CH(C_2H_5)-CH_2-$ |
| 4-F | $-CH_2O-$ | $-(CH_2)_2CH(CH_3)-CH_2-$ |
| 4-CH$_3$ | $-CH_2O-$ | $-(CH_2)_2CH(CH_3)-CH_2-$ |
| 4-CH$_3$ | $-CH_2O-$ | $-(CH_2)_2CH(C_2H_5)-CH_2-$ |
| 4-CH$_3$ | $-CH_2O-$ | $-CH_2-CH(CH_3)-CH_2-$ |
| 4-CH$_3$ | $-CH_2O-$ | $-(CH_2)_3CH(CH_3)-CH_2-$ |
| 4-CH$_3$ | $-CH_2O-$ | $-CH_2-CH(CH_3)(CH_2)_3-$ |
| 4-CH$_3$ | $-CH_2O-$ | $-CH(CH_3)(CH_2)_2-$ |
| 4-CH$_3$ | $-CH_2O-$ | $-(CH_2)_2CH(CH_3)-CH_2-$ |
| 4-CH$_3$ | $-CH_2O-$ | $-(CH_2)_2CH(CH_3)-CH_2-$ |

TABLE 1-continued

Examples of the present compound represented by the formula I

| $(R_1)_m$ | Y | Z |
|---|---|---|
| 4-CH$_3$ | —CH$_2$O— | —CH$_2$—CH(CH$_3$)—(CH$_2$)$_2$— |
| 3-CH$_3$ | —CH$_2$O— | —CH$_2$—CH(CH$_3$)—(CH$_2$)$_2$— |
| 3-CH$_3$ | —CH$_2$O— | —CH(CH$_3$)—CH$_2$— |
| 3-F, 4-OCH$_3$ | —(CH$_2$)$_3$— | —(CH$_2$)$_2$— |
| 2,4-(OCH$_3$)$_2$ | —(CH$_2$)$_3$— | —(CH$_2$)$_2$— |
| 2,5-(OCH$_3$)$_2$ | —(CH$_2$)$_3$— | —(CH$_2$)$_2$— |
| 3,4-(OCH$_3$)$_2$ | —(CH$_2$)$_3$— | —(CH$_2$)$_2$— |
| 3-OC$_2$H$_5$, 4-OCH$_3$ | —(CH$_2$)$_3$— | —(CH$_2$)$_2$— |
| 3,5-(OCH$_3$)$_2$ | —(CH$_2$)$_3$— | —(CH$_2$)$_2$— |
| 2,5-(CH$_3$)$_2$, 4-OCH$_3$ | —(CH$_2$)$_3$— | —(CH$_2$)$_2$— |
| 2,3-(CH$_3$)$_2$, 4-OCH$_3$ | —(CH$_2$)$_3$— | —(CH$_2$)$_2$— |
| 3,5-(OCH$_3$)$_2$ | —OCH$_2$— | —(CH$_2$)$_2$— |
| 3-Cl, 5-OCH$_3$ | —OCH$_2$— | —(CH$_2$)$_2$— |
| 2-OCH$_3$, 4-CH$_3$ | —OCH$_2$— | —(CH$_2$)$_2$— |
| 3,4-(OCH$_3$)$_2$ | —OCH$_2$— | —(CH$_2$)$_2$— |
| 3-OC$_2$H$_5$, 4-OCH$_3$ | —OCH$_2$— | —(CH$_2$)$_2$— |
| 2,3-(OCH$_3$)$_2$ | —CH$_2$O— | —(CH$_2$)$_2$— |
| 2,4-(OCH$_3$)$_2$ | —CH$_2$O— | —(CH$_2$)$_2$— |
| 3,4-(OCH$_3$)$_2$ | —CH$_2$O— | —(CH$_2$)$_2$— |
| 3-OC$_2$H$_5$, 4-OCH$_3$ | —CH$_2$O— | —(CH$_2$)$_2$— |
| 3-OCH$_3$, 4-OC$_2$H$_5$ | —CH$_2$O— | —(CH$_2$)$_2$— |
| 2,5-(OCH$_3$)$_2$ | —CH$_2$O— | —(CH$_2$)$_2$— |
| 4-Br | —(CH$_2$)$_3$— | —(CH$_2$)$_2$— |
| 4-Br | —(CH$_2$)$_3$— | —(CH$_2$)$_3$— |
| 4-Br | —(CH$_2$)$_3$— | —CH(CH$_3$)—CH$_2$— |
| 4-CH$_3$ | —CH$_2$O— | —CH$_2$—CH(CH$_3$)—(CH$_2$)$_3$— |
| 4-CH$_3$ | —CH$_2$O— | —(CH$_2$)$_4$CH(CH$_3$)—CH$_2$— |
| 4-F | —CH$_2$O— | —CH(CH$_3$)—(CH$_2$)$_4$— |
| 4-F | —CH$_2$O— | —CH(C$_2$H$_5$)—(CH$_2$)$_4$— |
| 4-CH$_3$ | —CH$_2$O— | —CH$_2$—CH(C$_2$H$_5$)—CH$_2$— |
| 4-CH$_3$ | —CH$_2$O— | —CH$_2$—CH(C$_2$H$_5$)—CH$_2$— |
| 4-CH$_3$ | —CH$_2$O— | —(CH$_2$)$_2$CH(C$_2$H$_5$)—(CH$_2$)$_2$— |
| 4-CH$_3$ | —CH$_2$O— | —(CH$_2$)$_3$CH(C$_2$H$_5$)—CH$_2$— |
| 4-CH$_3$ | —CH$_2$O— | —CH$_2$—CH(C$_2$H$_5$)—(CH$_2$)$_3$— |
| 2,3-(OCH$_3$)$_2$ | —(CH$_2$)$_3$— | —(CH$_2$)$_2$— |
| 2,6-(OCH$_3$)$_2$ | —(CH$_2$)$_3$— | —(CH$_2$)$_2$— |
| 2-OC$_2$H$_5$, 3-OCH$_3$ | —(CH$_2$)$_3$— | —(CH$_2$)$_2$— |
| 2,3-(OC$_2$H$_5$)$_2$ | —(CH$_2$)$_3$— | —(CH$_2$)$_2$— |
| 3-CH$_3$, 4-OCH$_3$ | —(CH$_2$)$_3$— | —(CH$_2$)$_2$— |
| 2-Br | —(CH$_2$)$_3$— | —(CH$_2$)$_2$— |
| 3-Br | —(CH$_2$)$_3$— | —(CH$_2$)$_2$— |
| 4-Br | —OCH$_2$— | —(CH$_2$)$_2$— |
| 4-Br | —OCH$_2$— | —(CH$_2$)$_3$— |
| 2-Br | —OCH$_2$— | —(CH$_2$)$_2$— |
| 3-Br | —OCH$_2$— | —(CH$_2$)$_2$— |
| 2,4-Br$_2$ | —OCH$_2$— | —(CH$_2$)$_2$— |
| 2-F, 4-Br | —OCH$_2$— | —(CH$_2$)$_3$— |
| 2-Cl, 4-Br | —OCH$_2$— | —(CH$_2$)$_2$— |
| 4-Br | —CH$_2$O— | —(CH$_2$)$_2$— |
| 3-Br | —CH$_2$O— | —(CH$_2$)$_2$— |
| 2-Br | —CH$_2$O— | —(CH$_2$)$_2$— |
| 3-Br, 4-F | —CH$_2$O— | (CH$_2$)$_2$ |

The compound of the present invention is effective for controlling acarines and mites including: House dust mites:
Epidermoptidae represented by (*Dermatophagoides farinae* Hughes) and *Dermatophagoides pteronyssinus*;
Acaridae represented by common grain mite (*Tyrophagus putrescentiae*) and brown legged grain mite (*Aleuroglyphus ovatus*); Glycyphagidae represented by *Glycyphagus privatus* Oudemans, furniture mite (*Glycyphagus domesticus*) and groceries mite (*Glycyphagus destructor*); Cheyletidae represented by *Cheyletus malaccensis* Oudemans and *Cheyletus fortis* Oudemans; Tarsonemidae;
Chortoglyphus spp.; and Haplochthoniidae.
Ticks and parasitic mites of domestic animals:
Ixodidae such as *Boophilus microplus*, etc.;
*Ornithonyssus bacoti* Hirst, fowl mite (*Ornithonyssus sylviarum* Canestrini et Fanzago, poultry mite (*Dermanyssus galinae*), etc.
The present compound may be used as an active ingredient as it is, however, the compound is usually formulated by adding other ingredient and/or an inert carrier. Examples of the formulation includes oil solutions, emulsifiable concentrates, wettable powders, flowables, dusts, aerosols, fumigants, smoking formulations, foggings, poison baits or mite-controlling sheets, each of which is obtained by mixing the present compound with a solid carrier, a liquid carrier, a gaseous carrier or bait or the like. A base material such as a porous ceramic plate or a non-woven fabric may be impregnated with the compound. Surfactants and other additives or auxiliary agents for the formulations are added to the compound if necessary. These formulations usually contain the present compound as an active ingredient in an amount of 0.01% to 95% by weight.

Examples of the solid carrier used for the formulation include fine powders or granules of clays such as kaolin clay, diatomaceous earth, synthetic hydrated silicon oxide, bentonite, fubasami clay and acid clay, talcs, ceramics, and other inorganic minerals such as sericite, quartz, sulfur, active carbon, calcium carbonate and hydrated silica. Examples of the liquid carrier include water, alcohols such as methanol and ethanol, ketones such as acetone and methylethyl ketone, aromatic hydrocarbons such as benzene, toluene, xylene, ethylbenzene, and methylnaphthalene, aliphatic hydro-carbons such as hexane, cyclohexane, kerosine, and gas oil, esters such as ethyl acetate and butyl acetate, alkylnitriles such as acetonitrile and isobutyronitrile, ethers such as diisopropyl ether and dioxane, acid amides such as N,N-dimethylformamide and N,N-dimethylacetamide, halogenated hydrocarbons such as dichloromethane, trichloroethane, and carbon tetrachloride, dimethyl sulfoxide, vegetable oils such as soybean oil and cottonseed oil. Examples of the gaseous carrier or propellant include CFCs (chlorofluorocarbons), butane gas, LPG (liquefied petroleum gas), dimethyl ether, and carbon dioxide or the like.

Examples of the surfactant include salts of alkyl sulfates, alkyl sulfonates and alkyl aryl-sulfonates; alkyl aryl ethers, polyoxyethylene compounds thereof, and polyethylene glycol ethers, polyhydric alcohol esters; and sugar alcohol derivatives.

Examples of additives or auxiliaries such as fixing agents and dispersing agents used for the formulations include casein, gelatin, polysaccharides such as starch, gum arabic, cellulose derivatives, alginic acid and lignin derivatives, bentonite, sugars, synthetic water-soluble polymers such as polyvinyl alcohol, polyvinyl pyrrolidone, and polyacrylic acid. Examples of the stabilizer include PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids and esters of fatty acids.

The base material of the poison baits includes a bait component such as grain powder, purified vegetable oil, sugar or crystalline cellulose, an antioxidant such as dibutylhydroxytoluene or nordihydroguaiaretic acid, a preservative such as dehydroacetic acid, a substance for preventing erroneous ingestion such as red pepper powder, an attractant flavor such as cheese flavor or onion flavor.

The formulations thus obtained is used as prepared or after diluted with water. The formulations of the invention may be used simultaneously with other acaricides, an insecticide (for example, d-allethrin or tetramethrin), an agent for controlling insects and mites (for example, d-phenothrin), a bactericide, a synergist or a animal feed under non-mixed conditions or pre-mixed conditions.

On the practical use of acaricides containing the present compound as an active ingredient, emulsifiable concentrates, wettable powders, or flowables such as water-based emulsions and suspensions are usually diluted with water to the concentration of 0.1 to 500 ppm. Granules, dusts, oil sprays, aerosols, fumigants, smoking formulations, foggings, poison baits, and mite-controlling sheets are used as prepared. The application rate of the formulations may be varied, i.e., optionally increased or decreased according to the type of the formulation, time, place, method of application, the type of mites, and the damage irrespective of the range described above.

The present invention will be further illustrated in more detail by production examples, formulation examples and biological test examples, although the invention is not limited in any sense to these examples.

Production examples of the compounds by the present invention are described first.

EXAMPLE 1

Production of the compound 3 by Method B

A mixture of 0.5 g of 7-phenylheptanol, 0.27 g of propiolic acid, 0.005 g of p-toluenesulfonic acid and 25 ml of benzene was refluxed with stirring for six hours while water formed was removed by a Dean-Stark water separator. After the reaction was completed, the reaction solution was washed successively with a 5% aqueous sodium bicarbonate solution and a saturated sodium chloride solution, and dried over anhydrous magnesium sulfate. After removal of the solvent under reduced pressure, the obtained residue was subjected to silicagel column chromatography to yield 0.368 g of 7-phenylheptyl propiolate (compound 3).

Yield 58%

$n_D^{22.7}$ 1.5021

EXAMPLE 2

Production of the compound 11 by Method B

A mixture of 1 g of 4-(4-methylphenoxy)butanol, 1.1 g of propiolic acid, 0.005 g of p-toluenesulfonic acid and 25 ml of benzene was refluxed with stirring for six hours while water formed was removed by a Dean-Stark water separator. After the reaction was completed, the reaction solution was washed successively with a 5% aqueous sodium bicarbonate solution and a saturated sodium chloride solution, and dried over anhydrous magnesium sulfate. After removal of the solvent under reduced pressure, the obtained residue was subjected to silicagel column chromatography to yield 1.15 g of 4-(4-methylphenoxy)butyl propiolate (compound 11).

Yield 89%

$n_D^{23.4}$ 1.5076

EXAMPLE 3

Production of the compound 16 by Method B

A mixture of 2 g of 2-benzyloxyethanol, 2.8 g of propiolic acid, 0.005 g of p-toluenesulfonic acid and 25 ml of benzene was refluxed with stirring for six hours while water formed was removed by a Dean-Stark water separator. After the reaction was completed, the reaction solution was washed successively with a 5% aqueous sodium bicarbonate solution and a saturated sodium chloride solution, and dried over anhydrous magnesium sulfate. After removal of the solvent under reduced pressure, the obtained residue was subjected to silicagel column chromatography to yield 2.39 g of 2-benzyloxyethyl propiolate (compound 16).

Yield 89%

$n_D^{24.5}$ 1.5120

EXAMPLE 4

Production of the compound 1 by Method A

With stirring, 1 gram of 5-phenylpentanol was added dropwise to a mixture of 0.25 g of sodium hydride (60% oil suspension) and 25 ml of dried benzene. The mixed solution is further stirred at ambient temperatures for one hour. A benzene solution of propiolic acid chloride is prepared by stirring a mixture of 0.62 g of sodium propiolate, 0.80 g of thionyl chloride, and 20 ml of dried benzene at ambient temperatures for five hours. The benzene solution of propiolic acid chloride thus prepared is added to the mixed solution, stirred at ambient temperatures for five hours, and refluxed for one hour. After the reaction is completed, the reaction solution is washed successively with water and a saturated sodium chloride solution, and dried over anhydrous magnesium sulfate. After removal of the solvent under reduced pressure, the obtained residue is subjected to silicagel column chromatography to yield 5-phenylpentyl propiolate (compound 1).

EXAMPLE 5

Production of the compound 2 by Method B

Under a nitrogen atmosphere at −20° C., a mixture of 1.3 g of dicyclohexylcarbodiimide, 0.051 g of 4-dimethylaminopyridine in 15 ml of dried ether is added dropwise, with stirring, to a mixture of 1 g of 6-phenylhexanol and 0.43 g of propiolic acid in 15 ml of dried ether. After the addition was over, the reaction solution was warmed to the room temperature and stirred at the room temperature for ten hours. After the reaction was completed, the reaction solution was filtered. The filtrate was washed twice with cold 1N hydrochloric acid and twice with a saturated sodium chloride solution, and dried over anhydrous magnesium sulfate. After removal of the solvent under reduced pressure, the obtained residue was subjected to silicagel column chromatography to yield 0.788 g of 6-phenylhexyl propiolate (compound 2).

Yield 61%

$n_D^{23.7}$ 1.5042

EXAMPLE 6

Production of the compound 10 by Method C

A mixture of 10 g of propiolic acid, 12 g of anhydrous sodium bicarbonate in 150 ml of anhydrous methanol was heated to 40° C. with stirring. When evolution of carbon dioxide ceased, the reaction mixture was cooled to a temperature 10° C. or less. The resultant precipitate was collected and dried under reduced pressure for two days. A mixture of 1 g of the sodium propiolate thus obtained and 2.64 g of 4-(2-methylphenoxy)butyl bromide in 30 ml of anhydrous N,N-dimethylformamide was heated at 110° C. under nitrogen atmosphere for four hours with stirring. After the reaction was completed, the reaction solution was poured into ice-water, and extracted twice with toluene. The combined toluene layer was washed successively with a saturated aqueous ammonium chloride solution and a saturated sodium chloride solution, and dried over anhydrous magnesium sulfate. After removal of the solvent under reduced pressure, the obtained residue was subjected to silicagel column chromatography to yield 0.937 g of 4-(2-methylphenoxy)butyl propiolate (compound 10).

Yield 37% mp. 49.1° C.

EXAMPLE 7

Production of the compound 3 by Method D

A mixture of 1 g of ethyl propiolate, 2.94 g of 7-phenylheptanol and 0.01 g of p-toluenesulfonic acid in 30 ml of benzene was refluxed for twelve hours. After removal of the solvent under reduced pressure, the obtained residue was subjected to silicagel column chromatography to yield 7-phenylheptyl propiolate (compound 3).

Table 2 shows exemplified compounds produced according to the invention (The table lists substituents of the compound of the formula I).

TABLE 2

The compounds of the formula I and their physicochemical constant

| Compound | $(R^1)_m$ | Y | Z | Physical constant |
|---|---|---|---|---|
| (1) | H | $-(CH_2)_3-$ | $-(CH_2)_2-$ | $n_D^{24.8}$ 1.5040 |
| (2) | H | $-(CH_2)_3-$ | $-(CH_2)_3-$ | $n_D^{23.7}$ 1.5042 |
| (3) | H | $-(CH_2)_3-$ | $-(CH_2)_4-$ | $n_D^{22.7}$ 1.5021 |
| (4) | H | $-(CH_2)_3-$ | $-(CH_2)_5-$ | $n_D^{23.9}$ 1.4989 |
| (5) | H | $-(CH_2)_3-$ | $-(CH_2)_6-$ | $n_D^{23.9}$ 1.4967 |
| (6) | H | $-OCH_2-$ | $-(CH_2)_2-$ | $n_D^{24.9}$ 1.5152 |
| (7) | H | $-OCH_2-$ | $-(CH_2)_3-$ | $n_D^{24.5}$ 1.5131 |
| (8) | H | $-OCH_2-$ | $-(CH_2)_4-$ | $n_D^{25.2}$ 1.5097 |
| (9) | 2,4-$(CH_3)_2$ | $-OCH_2-$ | $-(CH_2)_2-$ | $n_D^{22.3}$ 1.5095 |
| (10) | 2-$CH_3$ | $-OCH_2-$ | $-(CH_2)_3-$ | m.p. 49.1° C. |
| (11) | 4-$CH_3$ | $-OCH_2-$ | $-(CH_2)_3-$ | $n_D^{23.4}$ 1.5076 |
| (12) | 2,4-$(CH_3)_2$ | $-OCH_2-$ | $-(CH_2)_3-$ | $n_D^{24.4}$ 1.5110 |
| (13) | 2,6-$(CH_3)_2$ | $-OCH_2-$ | $-(CH_2)_3-$ | $n_D^{24.6}$ 1.5061 |

TABLE 2-continued

The compounds of the formula I and their physicochemical constant

| Compound | $(R^1)_m$ | Y | Z | Physical constant |
|---|---|---|---|---|
| (14) | 2,6-$(CH_3)_2$ | $-OCH_2-$ | $-(CH_2)_4-$ | $n_D^{24.4}$ 1.5039 |
| (15) | 2,6-$(i-C_3H_7)_2$ | $-OCH_2-$ | $-(CH_2)_3-$ | $n_D^{24.6}$ 1.4981 |
| (16) | H | $-CH_2O-$ | $-(CH_2)_2-$ | $n_D^{25.5}$ 1.5120 |
| (17) | H | $-CH_2O-$ | $-(CH_2)_3-$ | $n_D^{24.0}$ 1.5045 |
| (18) | 4-$CH_3$ | $-CH_2O-$ | $-(CH_2)_2-$ | $n_D^{23.7}$ 1.5106 |
| (19) | H | $-OCH_2-$ | $-(CH_2)_5-$ | $n_D^{25.2}$ 1.5069 |
| (20) | 4-$C_2H_5$ | $-OCH_2-$ | $-(CH_2)_2-$ | $n_D^{26.9}$ 1.5089 |
| (21) | 4-$CH_3$ | $-OCH_2-$ | $-(CH_2)_4-$ | m.p. 54.2° C. |
| (22) | 4-$C_2H_5$ | $-OCH_2-$ | $-(CH_2)_3-$ | $n_D^{25.2}$ 1.5090 |
| (23) | H | $-OCH_2-$ | $-CH(CH_3)-CH_2-$ | $n_D^{25.1}$ 1.5085 |
| (24) | 4-$CH_3$ | $-OCH_2-$ | $-CH(CH_3)-CH_2-$ | $n_D^{24.2}$ 1.5065 |
| (25) | H | $-OCH_2-$ | $-CH(CH_3)-(CH_2)_2-$ | $n_D^{22.7}$ 1.5081 |
| (26) | 4-$CH_3$ | $-OCH_2-$ | $-CH(CH_3)-(CH_2)_2-$ | $n_D^{22.6}$ 1.5062 |
| (27) | 2,6-$(CH_3)_2$ | $-OCH_2-$ | $-(CH_2)_2-$ | $n_D^{27.9}$ 1.5645 |
| *(28) | 4-$C_2H_5$ | $-CH_2O-$ | $-(CH_2)_2-$ | $n_D^{27.5}$ 1.5082 |
| (29) | H | $-CH_2O-$ | $-CH(CH_3)-CH_2-$ | $n_D^{28.9}$ 1.5011 |

*Compound 28 contains 2-$C_2H_5$ isomer in an amount of 30% by weight.

Formulation examples are described hereafter.

In the description below, parts represent parts by weight, and the compounds are shown by the numbers in Table 2.

Formulation Example 1

Emulsifiable concentrates

Ten parts of each of the compounds 1 to 29 are separately dissolved in 35 parts of xylene and 35 parts of dimethylformamide. Each of the obtained mixtures is mixed with 14 parts of polyoxyethylene styrylphenyl ether and 6 parts of calcium dodecylbenzenesulfonate, and stirred sufficiently to give 10% emulsifiable concentrate for each of the compounds.

Formulation Example 2

Wettable powders

Twenty parts of each of the compounds 1 to 29 are separately added to a mixture of 4 parts of sodium lauryl sulfate, 2 parts of calcium lignin sulfonate, 20 parts of synthetic hydrated silicon hydroxide fine powder and 54 parts of diatomaceous earth, and stirred with a mixer to give 20% wettable powder for each compound.

Formulation Example 3

Dusts

One part of each of the compounds 1 to 29 separately dissolved in an appropriate amount of acetone is mixed with 5 parts of synthetic hydrated silicon hydroxide fine powder, 0.3 part of PAP and 93.7 parts of clay, and stirred with a mixer and acetone is evaporated to give 1% dusts for each compound.

Formulation Example 4

Flowables (Water-based emulsions)

Twenty parts of each of the compounds 1 to 29 are separately mixed with 1.5 parts of sorbitan tri-oleate and 28.5 parts of an aqueous solution of 2 parts of polyvinyl alcohol, and the mixture is pulverized into fine particles of not greater than 3μ in diameter with a sand grinder if necessary. 20% Water-based emulsions for each compound is obtained by mixing each of the mixture with 40 parts of an aqueous solution of 0.05 part of xanthan gum and 0.1 part of aluminium magnesium silicate, and then mixed with 10 parts of propylene glycol with stirring.

Formulation Example 5

Oil solutions 0.1% Oil solutions for each of the compound 1 to 29 is obtained by dissolving 0.1 part of each of the compounds in 5 parts of xylene and 5 parts of trichloroethane and the solution is mixed with 89.9 parts of deodorized kerosine.

Formulation Example 6

Oil-based aerosol

Oil-based aerosol of each of the compounds 1 to 29 is obtained by filling an aerosol vessel with a mixture of 0.1 part of each of the compounds 1 to 29, 0.1 part of d-phenothrin and 10 parts of trichloroethane in 59.6 parts of deodorized kerosine, and then the vessel is set up with a valve, through which 30 parts of a propellant (liquefied petroleum gas) are charged under pressure.

Formulation Example 7

Oil-based aerosol

Oil-based aerosol of each of the compounds 1 to 29 is obtained by filling an aerosol vessel with a mixture of 0.1 part of each of the compounds 1 to 29, 0.2 parts of tetramethrin, 0.1 part of d-phenothrin and 10 parts of trichloroethane in 59.6 parts of deodorized kerosine, and then the vessel is set up with a valve, through which 30 parts of a propellant (liquefied petroleum gas) are charged under pressure.

Formulation Example 8

Oil-based aerosol

Oil-based aerosol of each of the compound 1 to 29 is obtained by filling an aerosol vessel with a mixture of 1 part of each of the compounds 1 to 29, 7 parts of kerosine and 32 parts of deodorized kerosine, and then the vessel was set up with a valve, through which 60 parts of a propellant (liquefied petroleum gas) are charged under pressure.

Formulation Example 9

Water-based aerosol

Water-based aerosol of each of the compounds 1 to 29 is obtained by filling an aerosol vessel with 50 parts of pure water and a mixture of 0.2 part of each of the compounds 1 to 29, 0.2 part of d-phenothrin, 5 parts of xylene, 3.6 parts of deodorized kerosine, and 1 part of an emulsifier Atmos 300 (registered trade mark by Atlas Chemical), and then the vessel is equipped with a valve, through which 40 parts of a propellant (liquefied petroleum gas) are charged under pressure.

Formulation example 10

Water-based aerosol

Water-based aerosol of each of the compounds 1 to 29 is obtained by filling an aerosol vessel with 50 parts of pure water and a mixture of 0.2 part of each of the compounds 1 to 29, 0.2 part of d-allethrin, 0.2 part of d-phenothrin, 5 parts of xylene, 3.4 parts of deodorized kerosine and 1 part of an emulsifier Atmos 300 (registered trade mark by Atlas Chemical), and then the vessel is set up with a valve, through which 40 parts of a propellant (liquefied petroleum gas) are charged under pressure.

Formulation Example 11

Heating smoke formulation

Heating smoke formulation of each of the compounds 1 to 29 is prepared by impregnating a porous ceramic plate (4.0 cm ×4.0 cm ×1.2 cm) with a solution prepared by dissolving 100 mg of each of the compounds 1 to 29 in an appropriate amount of acetone.

Formulation Example 12

Poison bait

A solution prepared by dissolving 10 mg of each of the compounds 1 to 29 separately in 0.5 ml of acetone is mixed homogeneously with 5 g of solid bait powder (Breeding Solid Feed Powder CE-2: trade name by Japan Clea Japan Corp.). Acetone was removed by air-drying to obtain 0.2% poison bait for each compound.

Formulation Example 13

Mite-controlling sheet

A solution of each of the compound 1 to 29 in acetone is added dropwise to non-woven fabric so that amount of the compound is 1 g/l $m^2$ after being air-dried to remove the acetone.

Formulation Example 14

Mite-controlling sheet

Each mite-controlling sheet is prepared by impregnating filter paper with an acetone solution containing each of the compounds 1 to 29 so that the amount of the compound is 1 g/l $m^2$ after being air-dried to remove the acetone.

The following biological tests were performed to demonstrate that each compound of the present invention works as an active ingredient of an acaricide. In the description below, the compounds are shown by the numbers in Table 2.

Biological Test Example 1

A piece of filter paper (diameter: 4 cm) was impregnated uniformly with an acetone solution of the present compound so that the amount of the impregnated compound was 0.8 g/$m^2$ after being air-dried. Approximately twenty heads of mites (*Tyrophagus putrescentiae, Dermatophagoides farinae* Hughes and *Dermatophagoides pteronyssinuis*) were put on the surface of the treated filter paper. An adhesive substance was applied on the circumference of the filter paper for preventing escape. After one day, the mortality was examined. The results for *Tyrophagus putrescentiae, Dermatophagoides farinae* Hughes and *Dermatophagoides pteronyssinus* are shown in Table 3, Table 4, and Table 5, respectively.

TABLE 3

| Activity against *Tyrophagus putrescentiae* | |
|---|---|
| Compound | Mortality (%) |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |

TABLE 3-continued

Activity against *Tyrophagus putrescentiae*

| Compound | Mortality (%) |
|---|---|
| (14) | 100 |
| (15) | 100 |
| (16) | 100 |
| (17) | 100 |
| (18) | 100 |
| (19) | 100 |
| (20) | 100 |
| (21) | 100 |
| (22) | 96 |
| (23) | 100 |
| (24) | 100 |
| (25) | 100 |
| (26) | 100 |
| (27) | 100 |
| (28) | 100 |
| (29) | 100 |
| No treatment | 0 |

TABLE 4

Activity against *Dermatophagoides farinae* Hughes

| Compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (21) | 100 |
| (22) | 100 |
| (23) | 100 |
| (24) | 100 |
| (25) | 100 |
| (26) | 96 |
| (27) | 86 |
| (28) | 100 |
| (29) | 100 |
| No treatment | 0 |

TABLE 5

Activity against *Dermatophagoides pteronyssinus*

| Compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| No treatment | 0 |

Biological Test Example 2

A piece of filter paper (diameter: 4 cm) was impregnated uniformly with an acetone solution of the compound sample so that the amount of the compound was 0.8 g/m$^2$ after being air-dried. After seven days, approximately twenty heads of mites (*Dermatophagoides pteronyssinus*) were put on the surface of the treated filter paper. An adhesive substance was applied on the circumference of the filter paper for preventing escape. After one day, the mortality was examined. The results are shown in Table 6.

TABLE 6

Residual activity against *Dermatophagoides pteronyssinus*

| Compound | Mortality (%) |
|---|---|
| (1) | 95 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 92 |
| (14) | 100 |
| (15) | 95 |
| (16) | 83 |
| (17) | 100 |
| (18) | 100 |
| (19) | 100 |
| (20) | 100 |
| (21) | 100 |
| (22) | 100 |
| (23) | 100 |
| (24) | 100 |
| (25) | 100 |
| (26) | 94 |
| (27) | 100 |
| (28) | 97 |
| (29) | 82 |

Biological Test Example 3

A piece of filter paper (diameter: 4 cm) was placed in an aluminum plate and an adhesive substance was applied on the circumference of the filter paper for preventing escape. Fifty to a hundred heads of mites (*Tyrophagus putrescentiae*) were put with little feed on the filter paper. Three sets of such filter paper with mites were placed on three corners (approximately 30 cm from the wall) in a floor of a peat grady chamber (1.8 m ×1.8 m ×1.8 m). A porous ceramic plate (4 cm ×4 cm ×1.2 cm) impregnated with an acetone solution of the present compound (concentration: 55 mg/m³) was heated at 175° C. with an electric heater placed on the center of the floor of the chamber. After twenty-four hours, the mortality was examined. The results are shown in Table 7.

TABLE 7

| \multicolumn{2}{c}{Fumigating activity against *Tyrophagus putrescential*} |  |
| --- | --- |
| Compound | Mortality (%) |
| (1) | 76 |
| (2) | 73 |
| (3) | 96 |
| (11) | 79 |
| Phenyl salicylate | 28% |
| No treatment | 0 |

What is claimed is:

1. A propiolate ester compound represented by the formula I:

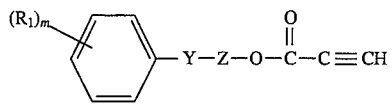

wherein $R_1$ represents a hydrogen atom, a halogen atom, a $C_1$–$C_4$ alkyl group or a $C_1$–$C_4$ alkoxy group;

m is an integer of 1 to 5;

Y represents —$CH_2CH_2CH_2$—, —$OCH_2$—, or —$CH_2O$—;

Z represents a $C_2$–$C_6$ alkylene group which may be substituted with a $C_1$–$C_4$ alkyl group; and $R_1$ may be the same or different, when m is an integer of larger than 1.

2. A compound according to claim 1, wherein $R_1$ represents a hydrogen atom and m is an integer of 1.

3. A compound according to claim 1, wherein $R_1$ represents a $C_1$–$C_4$ alkyl group and m is an integer of 1.

4. A compound according to claim 1, which is 7-phenylheptyl propiolate.

5. A compound according to claim 1, which is 4-(4-methylphenoxy)butyl propiolate.

6. A compound according to claim 1, which is 2-benzyloxyethyl propiolate.

7. A compound according to claim 1, which is 5-phenylpentyl propiolate.

8. A compound according to claim 1, which is 6-phenylhexyl propiolate.

9. A compound according to claim 1, which is 4-(2-methylphenoxy)butyl propiolate.

10. A composition for controlling acarines and mites which comprises an effective amount of a propiolate ester compound according to claim 1 and an inert carrier.

11. A method for controlling acarine and mite which comprises applying an effective amount of a propiolate ester compound according to claim 1.

12. A method comprising applying a propiolate ester compound represented by the formula (I)

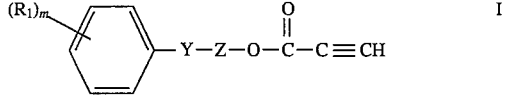

wherein $R_1$ represents a hydrogen atom, a halogen atom, a $C_1$–$C_4$ alkyl group or a $C_1$–$C_4$ alkoxy group;

m is an integer of 1 to 5;

Y represents —$CH_2CH_2CH_2$, —$OCH_2$—, or —$CH_2O$—;

Z represents a $C_2$–$C_6$ alkylene group which may be substituted with a $C_1$–$C_4$ alkyl group; and $R_1$ may be the same or different, when m is an integer of larger than 1, as an agent for controlling acarines and mites.

* * * * *